US011246722B2

(12) United States Patent
Christenson et al.

(10) Patent No.: US 11,246,722 B2
(45) Date of Patent: Feb. 15, 2022

(54) PROSTHETIC ATTACHMENT DEVICE FOR OSSEOINTEGRATED IMPLANTS

(71) Applicant: Motion Control, Inc., Salt Lake City, UT (US)

(72) Inventors: Jeffery David Christenson, West Valley City, UT (US); Edwin Kay Iversen, Salt Lake City, UT (US); Kent Nelson Bachus, Salt Lake City, UT (US); Heath Byron Henninger, Salt Lake City, UT (US); Alex Drew, Austin, TX (US)

(73) Assignee: Motion Control, Inc., Salt Lake City, UT (US)

( * ) Notice: Subject to any disclaimer, the term of this patent is extended or adjusted under 35 U.S.C. 154(b) by 231 days.

(21) Appl. No.: 16/218,157

(22) Filed: Dec. 12, 2018

(65) Prior Publication Data

US 2019/0175370 A1 Jun. 13, 2019

Related U.S. Application Data

(60) Provisional application No. 62/597,881, filed on Dec. 12, 2017.

(51) Int. Cl.
*A61F 2/76* (2006.01)
*A61F 2/78* (2006.01)
(Continued)

(52) U.S. Cl.
CPC ............... *A61F 2/78* (2013.01); *A61F 2/68* (2013.01); *A61F 2/76* (2013.01);
(Continued)

(58) Field of Classification Search
CPC ...... A61F 2/76; A61F 2/78; A61F 2002/5083; A61F 2002/30482; A61F 2002/305
See application file for complete search history.

(56) References Cited

U.S. PATENT DOCUMENTS

2007/0032884 A1\* 2/2007 Veatch ............... A61F 2/78
623/64
2008/0288087 A1\* 11/2008 Bachus ............... A61F 2/76
623/36

(Continued)

*Primary Examiner* — Brian E Pellegrino
(74) *Attorney, Agent, or Firm* — Thorpe North and Western, LLP (57) ABSTRACT

Technology is described for easy and safe attachment of a prosthetic limb to a percutaneous post that has been osseointegrated into the remnant limb of an individual with limb loss. A quick-disconnect device for a prosthetic limb can comprise a percutaneous post support assembly comprising a post locking assembly attached to a percutaneous post. A roller support can be coupled to the percutaneous post support assembly and can support torsional breakaway rollers. A release housing assembly can be coupled to the percutaneous post support assembly, and can comprise a limb support housing supporting a limb attachment structure to support a prosthetic limb. The release housing assembly comprises a torsional breakaway spring. The plurality of torsional breakaway rollers are each biased to the torsional breakaway spring to generate a spring force to restrict or limit rotation of the percutaneous post support assembly. Other breakaway springs and rollers are provided for bending release and axial release.

16 Claims, 9 Drawing Sheets

(51) Int. Cl.
*A61F 2/68* (2006.01)
*A61F 2/30* (2006.01)
*A61F 2/50* (2006.01)

(52) U.S. Cl.
CPC .............. *A61F 2002/30329* (2013.01); *A61F 2002/5083* (2013.01); *A61F 2002/6845* (2013.01); *A61F 2002/7868* (2013.01); *A61F 2002/7887* (2013.01)

(56) References Cited

U.S. PATENT DOCUMENTS

2011/0257765 A1\* 10/2011 Evans .................... A61F 2/70
  623/57
2017/0027720 A1\* 2/2017 Pedtke .................... A61F 2/78
  623/33

\* cited by examiner

PROSTHETIC ATTACHMENT DEVICE FOR OSSEOINTEGRATED IMPLANTS

BACKGROUND

Prostheses (or prosthetics) are artificial devices that replace body parts (e.g., fingers, hands, arms, legs). Generally, prostheses may be used to replace body parts lost by injury or missing from birth. In the past, prostheses have typically connected to a person's body using socket that can receive a remnant limb and is connectable to a prosthetic limb.

Prostheses can also be connected to a person's body using an osseointegrated implant where a metal implant may be used that is implanted into the bone of the remnant limb and passes through the soft skin and outside a person's body. Percutaneous posts may be implanted (osseointegrated) into the remnant limb of individuals with limb-loss or missing limbs and may be used to attach to a prosthesis. In some situations, a porous titanium coating may be used on the implant to enable a person's skin and bone to grow into the coating and better bind to the osseointegrated implant or percutaneous post.

DETAILED DESCRIPTION

Reference will now be made to the examples illustrated in the drawings, and specific language will be used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure are to be considered within the scope of the description.

The present disclosure sets forth technology for easy and safe attachment of a prosthetic limb to an osseointegrated implant (e.g., a percutaneous post) that has been osseointegrated into the remnant limb of an individual with limb loss. For example, devices and structures are described to enable an easy and safe attachment system for upper and lower limb prostheses to a percutaneous post that has been osseointegrated into the remnant limb of an individual with limb loss.

A quick-disconnect device or safety release mechanism provides an easy attach and disconnect connection system for the percutaneous post of an upper or lower limb prosthesis system. The device or mechanism provides compliance and a breakaway system to protect the individual with limb loss and prosthesis from overload or damage to the bone interface in the individual, as further detailed below.

This quick-disconnect device or safety release mechanism may include a number of structures, features and functions, as exemplified below with reference to the figures. One function is the ability to easily attach and remove a prosthesis using the quick-disconnect device. The attachment may be accomplished via a lever or cam mechanism (e.g., FIGS. 1B and 2B). A second function may be breakaway or release protection from axial, bending, and the torsional force overloading. This technology or system protects the abutment/bone interface from loads that could cause trauma, loosening, or bone fracture. The loads at which the device breaks-away can be adjustable by replacing springs or other compliant structures (e.g., 148, 158, and/or 172, as discussed below and in FIG. 3A), and can be adjustable by modifying incline planes and cam surfaces, as discussed herein. When the device breaks-away, the device may be mechanically reset by the user. A third function may be compliance in three degrees of freedom (i.e., axial, bending and torsional). Such compliance may help to reduce shock loading to the remnant limb and provides a more natural soft feel to the prosthesis. The compliance can be provided by springs and rollers acting on cam or curved surfaces, as exemplified below.

This present technology can also allow a prosthesis to be mounted to a quick-disconnect device that can be adjusted and aligned in all three directions and all three orientations (i.e., axially x, y, z, and rotationally yaw, pitch and roll). This can be accomplished using a pyramid attachment device (e.g., support 108 discussed below) distal to the osseointegrated percutaneous post that can be mounted via screws in slots and spacers that allow lateral and rotational adjustability (e.g., x, y, z and roll). The pyramid attachment device can allow for yaw and pitch adjustments.

Quick-Disconnect Devices

Figure 1A:
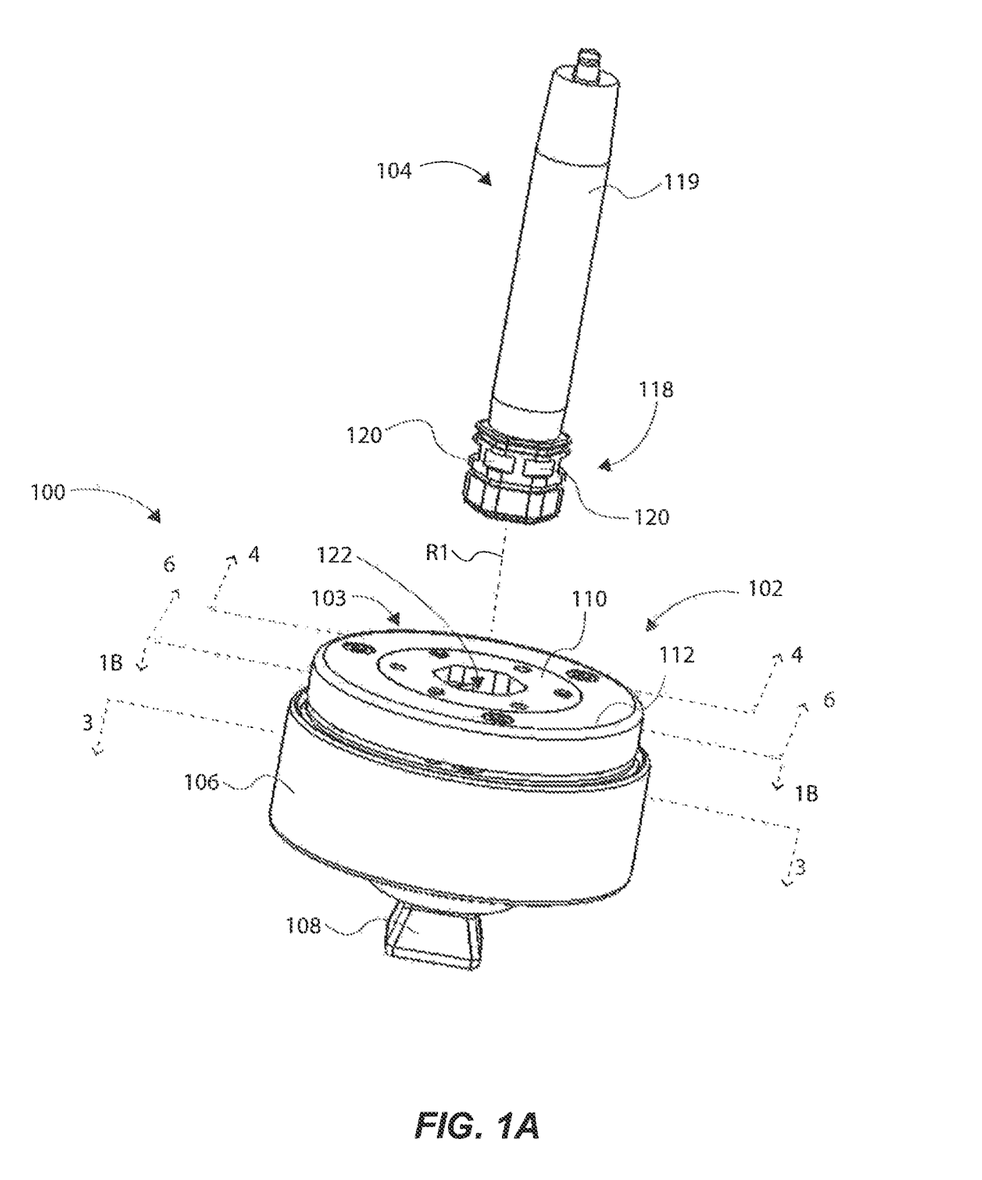
FIG. 1A is an isometric view of a quick-disconnect device, and a percutaneous post disconnected from the quick-disconnect device, in accordance with an example of the present disclosure.
Figure 1B:
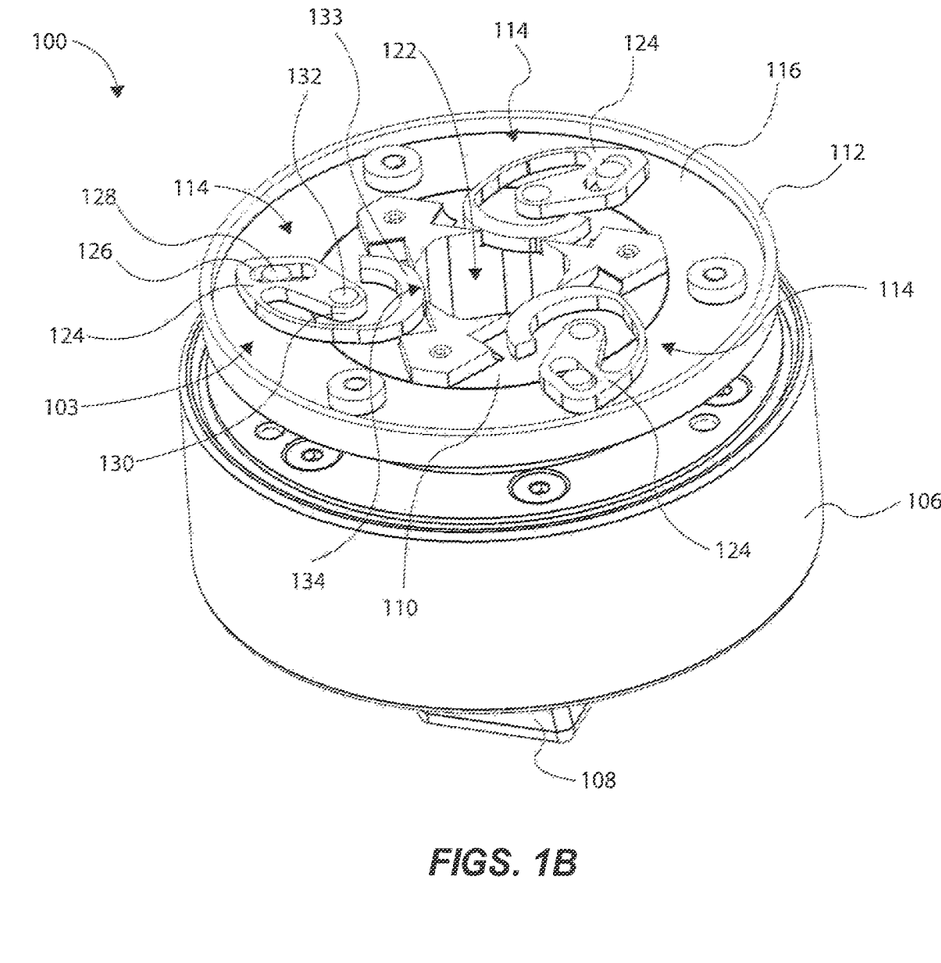
FIG. 1B is a cross sectional view of the quick-disconnect device of FIG. 1A, and taken along lines 1A-1A, in accordance with an example.

FIGS. 1A and 1B illustrate a quick-disconnect device 100 for attaching a prosthetic limb to a user, in one example of the present disclosure. The quick-disconnect device 100 can comprise a percutaneous post support assembly 102 comprising a post locking assembly 103 operable to attach the quick-disconnect device 100 to a percutaneous post 104 (i.e., an osseointegrated post installed partially into a human bone). The quick-disconnect device 100 can comprise a limb support housing 106 supporting a limb attachment structure 108 operable to support a prosthetic limb (not shown) and to align the prosthetic limb.

The percutaneous post support assembly 102, and the post locking assembly 103, can comprise a post receiving structure 110 and a structural support housing 112 rotatably interfaced to each other about an axis of rotation R1 to facilitate operation of a cam system or mechanism 114 (FIG. 1B), as detailed below. The post locking assembly 103 can further comprise a cam support plate 116 attached to the structural support housing 112 by three fasteners. As shown in FIG. 1A, the percutaneous post 104 can include an attachment end 118 (e.g., hexagon shaped) having a plurality of lateral slots 120. The attachment end 118 can extend out from remnant limb, while the other end 119 can be supported in and by the remnant limb. The attachment end 118 can be inserted into an aperture 122 of the post receiving structure 110, and then the structural support housing 112 can be rotated (by hand) relative to the post receiving structure 110 to lock the quick-disconnect device 100 to the percutaneous post 104 via the cam mechanism 114.

More specifically, as shown in FIG. 1B the cam mechanism 114 can comprise a plurality of movable cams 124 (3x) each having a slot 126 that slidably receives a support pin 128 coupled to the cam support plate 116, and each movable cam 124 having one end 130 pivotally supported by the post receiving structure 110 via a pivot pin 132. Each movable cam 124 can further comprise a cam end 133 having a radial or cam surface 134 proximate the aperture 122. Accordingly, upon rotation (by hand) of the structural support housing 112 relative to the post receiving structure 110, the movable cams 124 collectively move or pivot about pivot pins 132 while the slots 126 slide along the support pins 128, which causes the cam ends 133 to inwardly move or rotate into the aperture 122 to be seated in respective lateral slots 120 of the attachment end 118 (FIG. 1A) of the percutaneous post 104 to lock the quick-disconnect device 100 to the percutaneous post 104. As can be appreciated, opposite rotation of the structural support housing 112 relative to the post receiving structure 110 will unlock the quick-disconnect device 100 from the percutaneous post 104. The cam mechanism 114 may reduce play between the device 100 and the percutaneous post 104, and can provide a solid and secure feel when a prosthesis is attached to the limb attachment structure 108.

Figure 2A:
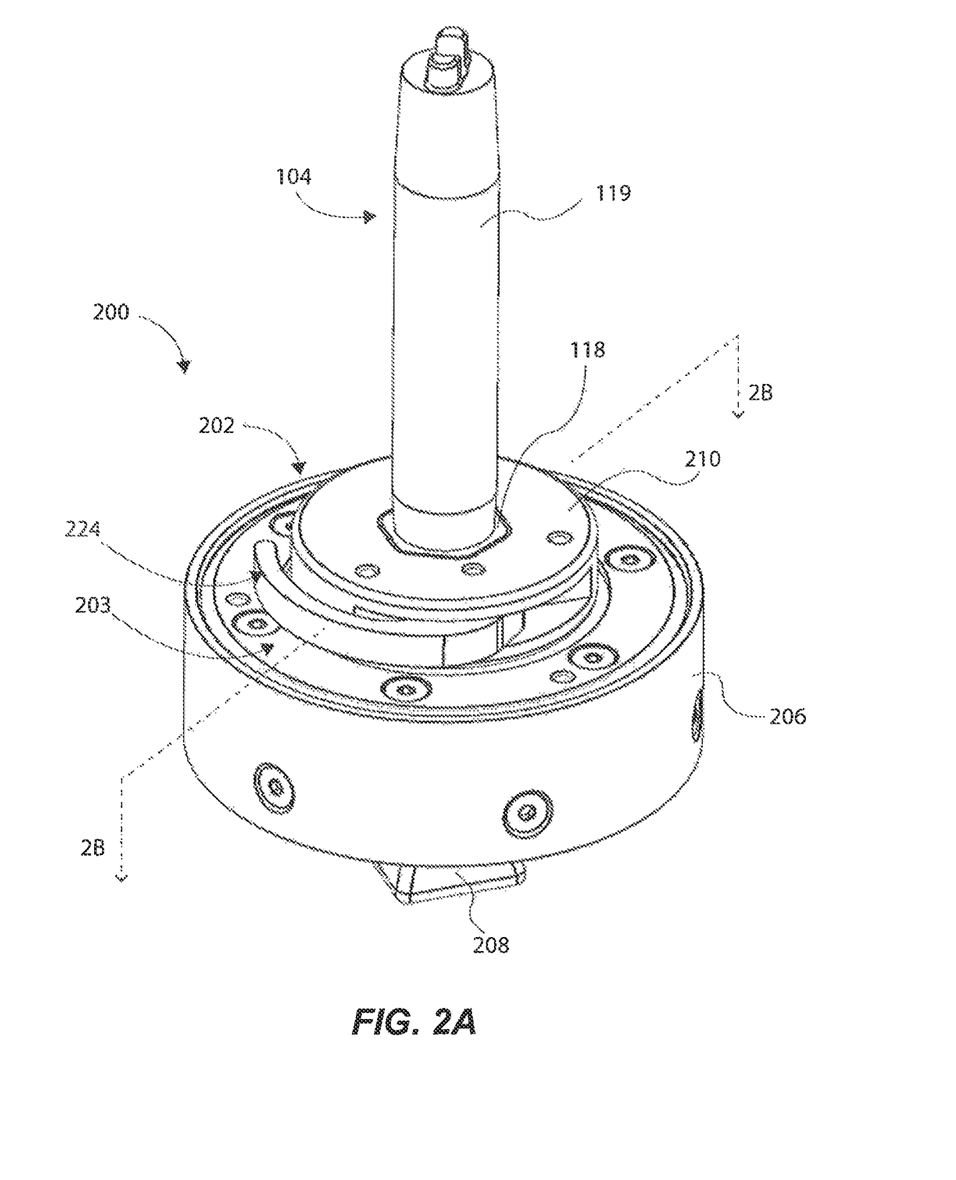
FIG. 2A is an isometric view of a quick-disconnect device attached to a percutaneous post, in accordance with an example of the present disclosure.
Figure 2B:
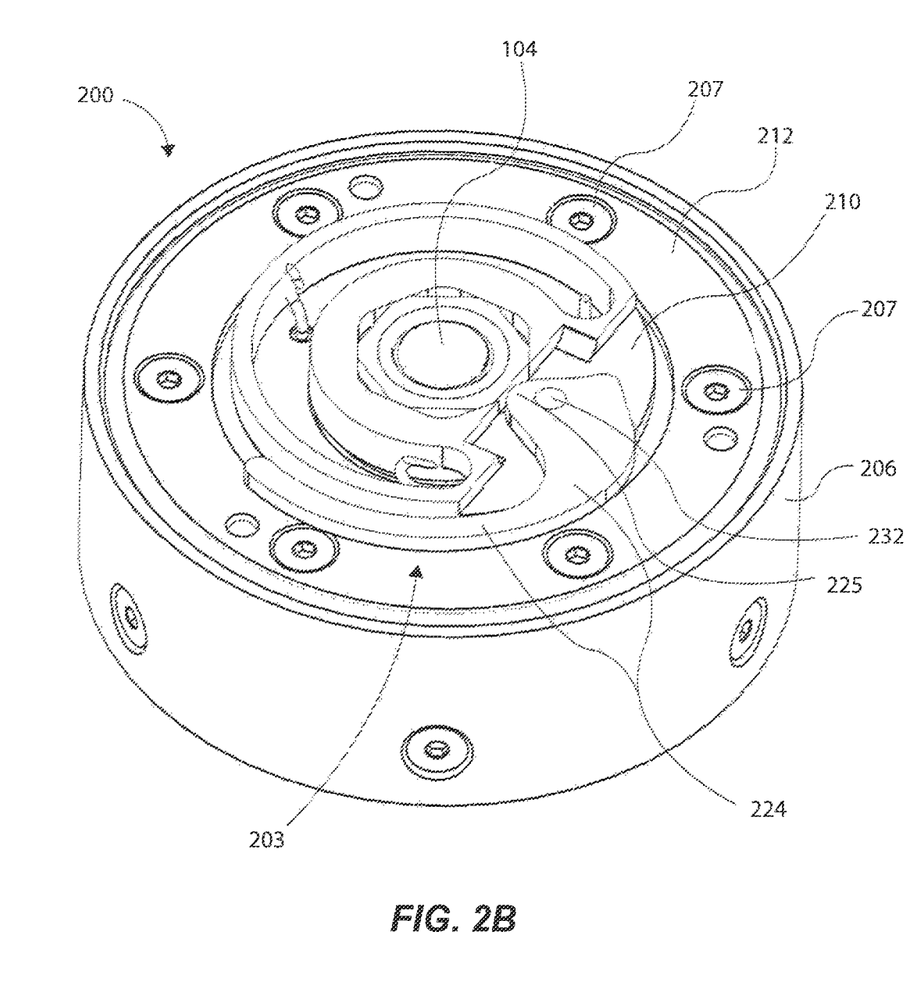
FIG. 2B is a cross sectional view of the quick-disconnect device of FIG. 2A, and taken along lines 2A-2A, in accordance with an example.

FIGS. 2A and 2B illustrate a quick-disconnect device 200 for a prosthetic limb, in one example of the present disclosure. The quick-disconnect device 200 can comprise a percutaneous post support assembly 202 comprising a post locking assembly 203 operable to attach the quick-disconnect device 200 to the percutaneous post 104. The quick-disconnect device 200 can comprise a limb support housing 206 supporting a limb attachment structure 208 operable to support a prosthetic limb (not shown). The post locking assembly 203 can comprise a post receiving structure 210 and a structural support housing 212, which can be fastened to the limb support housing 206 via six fasteners 207. The post receiving structure 210 can support a movable lever 224 operable to lock or unlock the quick-disconnect device 200 to the percutaneous post 104. Accordingly, the movable lever 224 can be pivotally coupled to the post receiving structure 210 by a support pin 232 (FIG. 2B), such that a user can grab the movable lever 224 and pull the movable lever 224 away from the percutaneous post 104 to unlock it, and then rotate the lever 224 toward the percutaneous post 104 to lock the percutaneous post 104 to the quick-disconnect device 200. Thus, the lever 224 may have a locking interface surface 225 that may be received by one of the lateral slots 120 of the percutaneous post 104 to facilitate locking and unlocking.

Figures 3A, 3B:
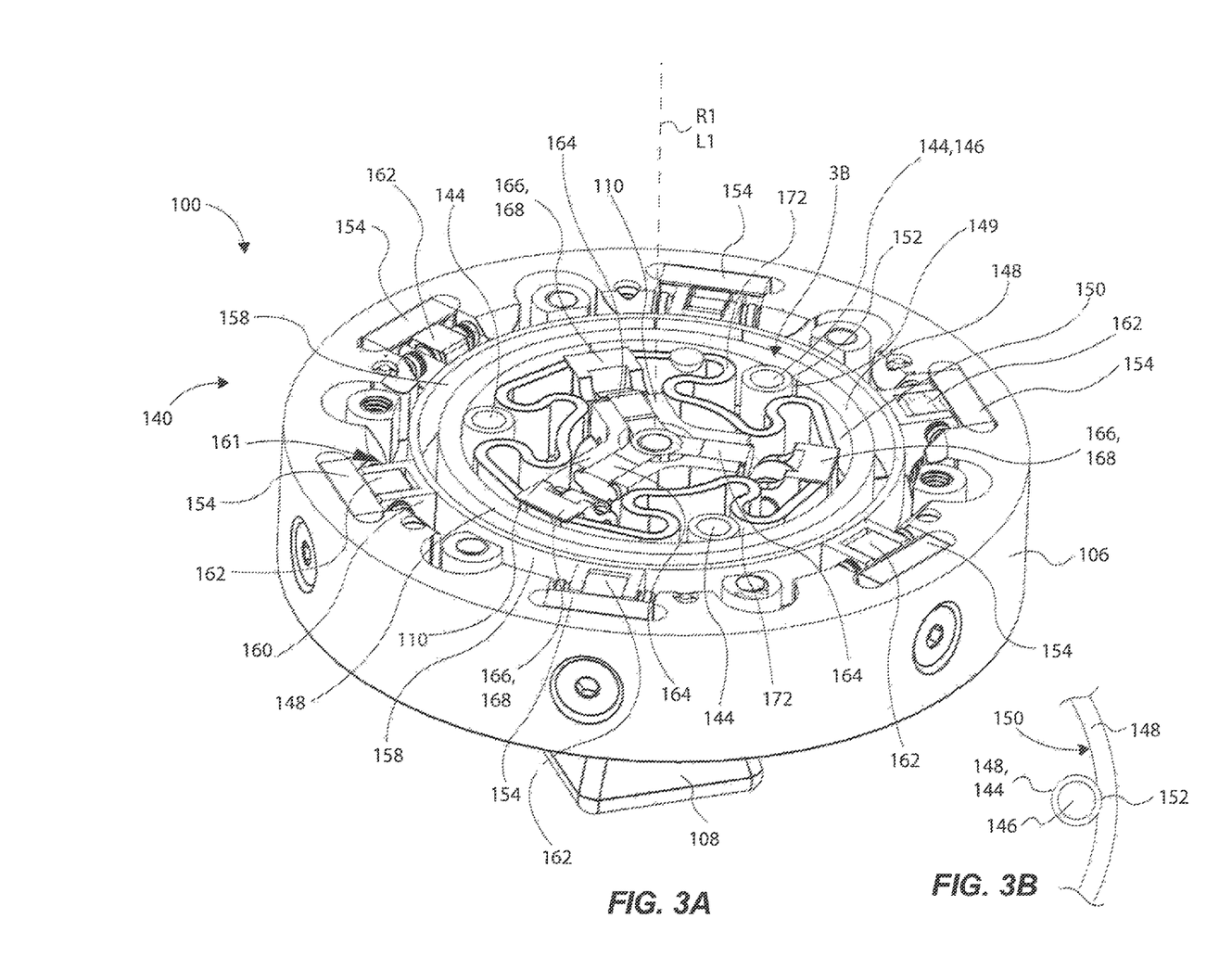
FIG. 3A is a cross sectional view of the quick-disconnect device of FIG. 1A, and taken along lines 3A-3A, in accordance with an example.
FIG. 3B is a top down view of a roller and a torsional breakaway spring of the quick-disconnect device of FIG. 3A, in accordance with an example.
Figure 4:
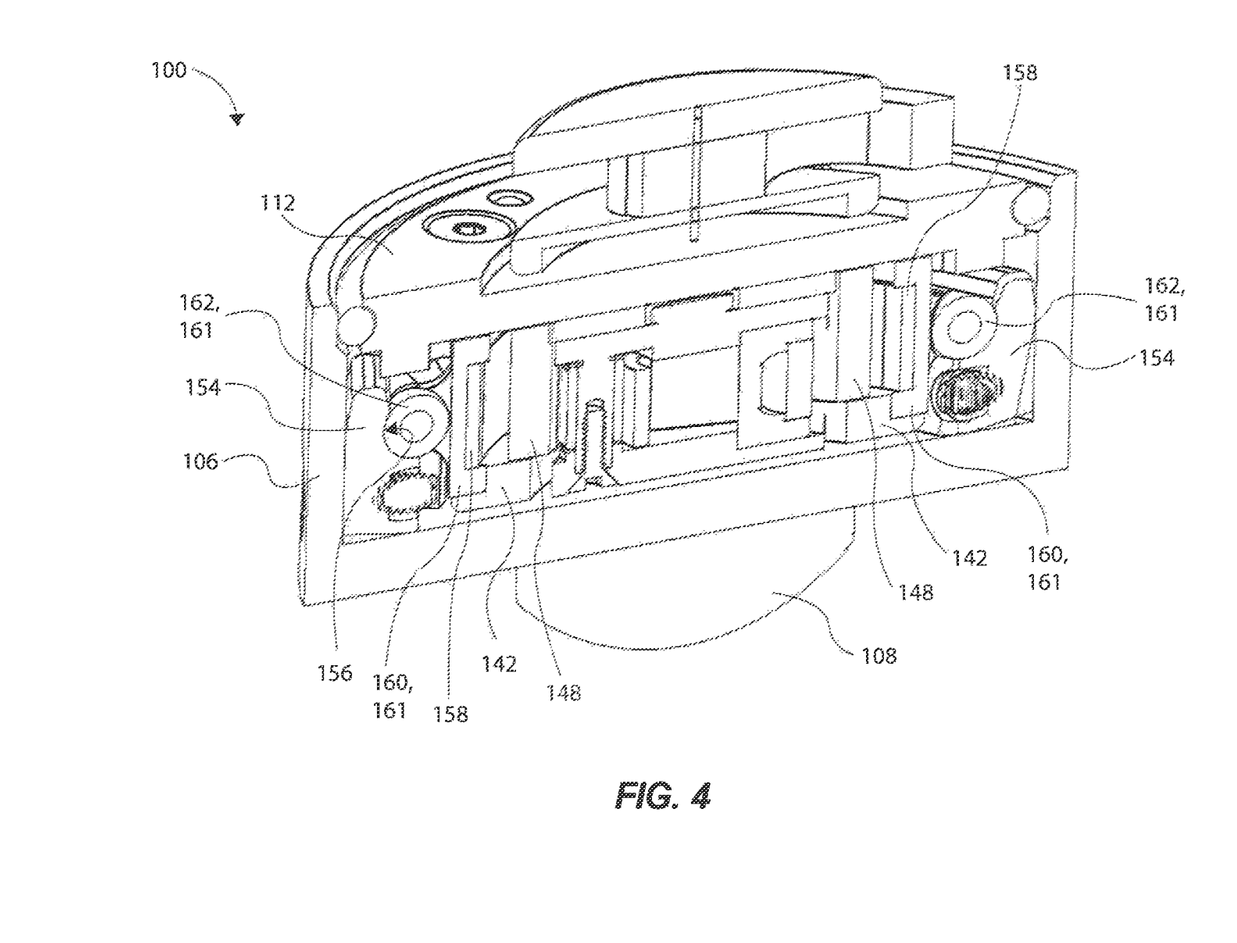
FIG. 4 is a cross sectional view of the quick-disconnect device of FIG. 1A, and taken along lines 4-4, in accordance with an example.
Figure 6:
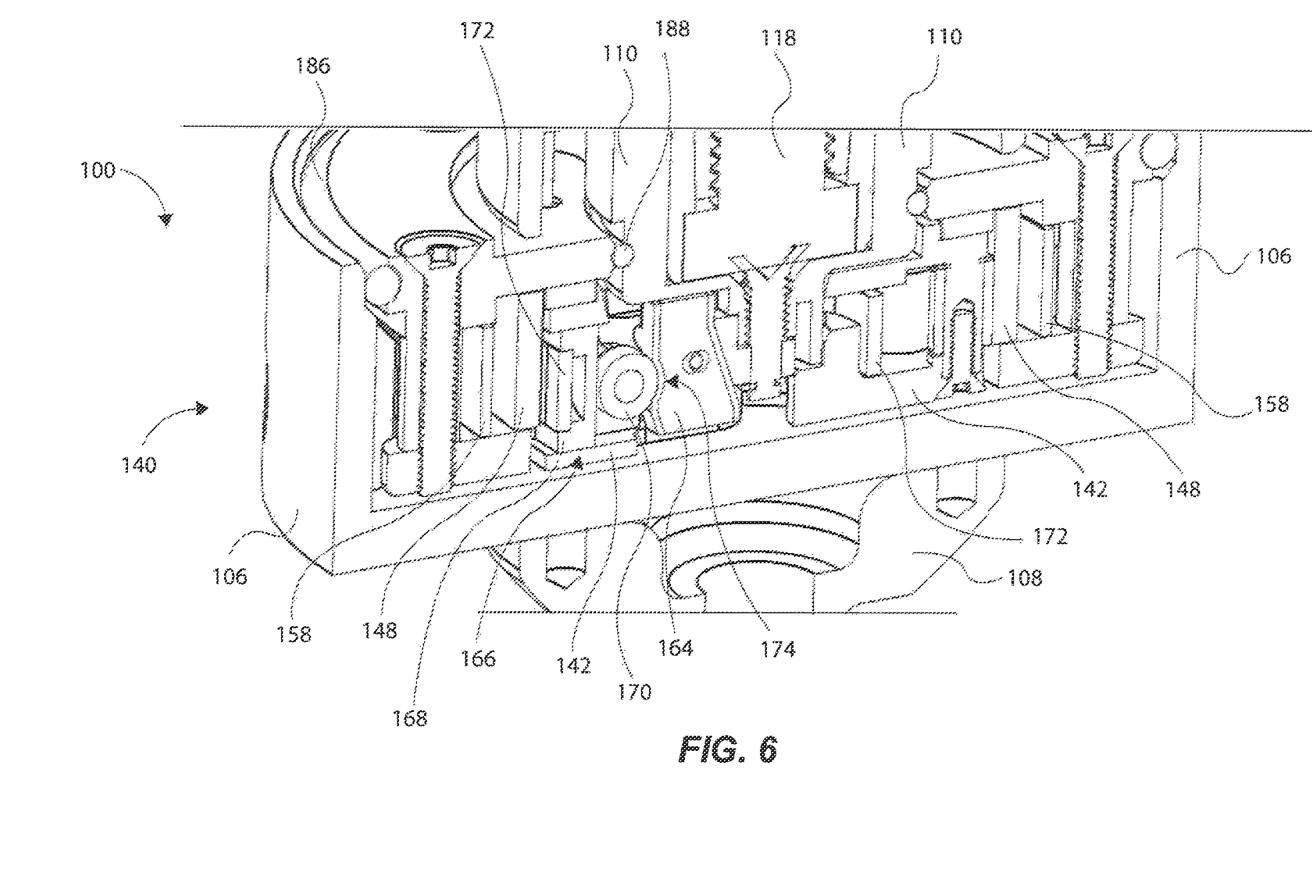
FIG. 6 is a cross sectional view of the quick-disconnect device of FIG. 1A, and taken along lines 6-6, in accordance with an example.

FIGS. 3A, 4, and 6 provide cross-sectional views that show various components of the quick-disconnect device 100 of FIGS. 1A and 1B. It should be appreciated that the discussion of the components of FIGS. 3A, 4, and 6, and their functionality, can also be incorporated with the quick-disconnect device 200 of FIG. 2A.

Figure 5:
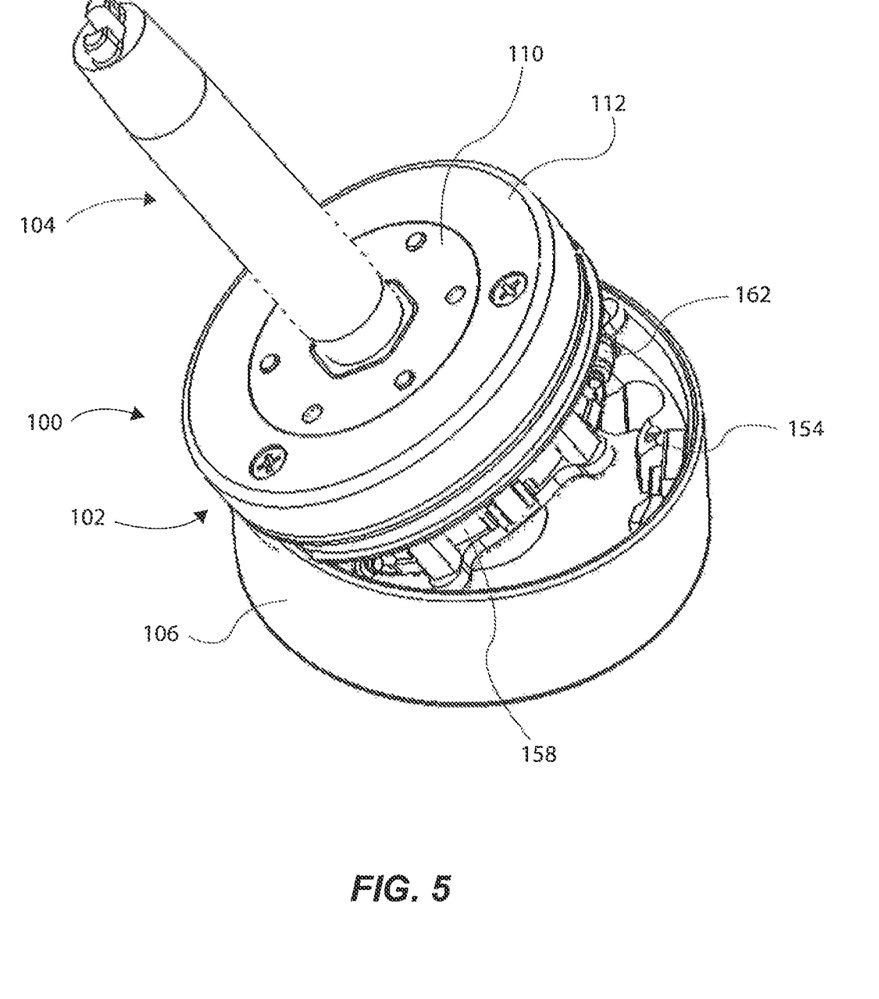
FIG. 5 is an isometric view of the quick-disconnect device of FIG. 1A, and showing a bending release of a portion of the quick-disconnect device from the percutaneous post, in accordance with an example.

As an overview, the quick-disconnect device 100 can be operated to facilitate axial release of the limb support housing 106 from the percutaneous post 104 (see FIG. 7), and to facilitate torsional release of the limb support housing 106 relative to the percutaneous post 104 (see FIGS. 2A and 2B), and to facilitate bending or rotational moment release of the limb support housing 106 from the percutaneous post 104 (see FIG. 5). Moreover, the quick-disconnect device 100 can provide some level of compliance axially, torsionally, and rotationally between the limb support housing 106 and the percutaneous post 104, which can provide a more natural (and less rigid) feeling between a prosthesis and the percutaneous post 104, as further detailed below.

More specifically, regarding the torsional release or restriction, the quick-disconnect device 100 can comprise a release housing assembly 140 (FIG. 3A), which can include the limb support housing 106, and a number of other components discussed below. Thus, the release housing assembly 140 can comprise a roller support 142 (FIGS. 4 and 6) coupled to the post receiving structure 110 of the percutaneous post support assembly 102. The roller support 142 can be a circular plate or body that is rotationally fixed with respect to the post receiving structure 110, so that the roller support 142 and post receiving structure 110 can rotate relative to the limb support housing 106 about an axis of rotation R1. The roller support 142 can support a plurality of torsional breakaway rollers 144 (FIG. 3A) that each comprise a support shaft 146 and a roller 149 (FIG. 3B) that rotates about the support shaft 146. The torsional breakaway rollers 144 can be oriented parallel to, and rotate relative to, the axis of rotation R1.

The release housing assembly 140 can further comprise a torsional breakaway spring 148 that can be rotationally fixed to, and supported by, the limb support housing 106, such that the torsional breakaway spring 148 and the limb support housing 106 are rotatable relative to the roller support 142 (and the percutaneous post 104). The torsional breakaway spring 148 can be in the shape of a ring having a relatively large inner diameter and outer diameter relative to the thickness of the wall of the torsional breakaway spring 148, and can have a rectangular cross sectional area (or other shape, such as square, oval, polygon, irregular, etc.). Thus, in one example, the torsional breakaway spring 148 can be considered "a ring spring" that is shaped like a ring and has, or defines, some amount of spring effect or result, as further detailed below. The torsional breakaway spring 148 can comprise an inner surface 150 (FIG. 3B), and the plurality of torsional breakaway rollers 144 may be biased to the inner surface 150 to generate an outward force to the torsional breakaway spring 148 to limit or restrict rotation of the torsional breakaway spring 148 (and the limb support housing 106) relative to the percutaneous post 104. That is, upon rotation of the torsional breakaway spring 148 relative to the percutaneous post 104 about the axis of rotation R1, the torsional breakaway rollers 144 may roll along the inner surface 150 while applying the outward biasing force, so that a certain amount of torque is used to rotate the torsional breakaway spring 148 relative to the percutaneous post 104 about the axis of rotation R1. This provides a safety feature, so that a prosthetic limb cannot freely rotate relative to the percutaneous post 104 unless the selected amount of torque is applied (e.g., 10-40 ft. lbs.), which can prevent injury to the user if an increased torque (e.g., higher than a threshold amount) is applied between the prosthesis limb and the percutaneous post 104.

In one example, the inner surface 150 of the torsional breakaway spring 148 can comprise a recessed portion 152 (FIG. 3B) that acts as a seat for one of the torsional breakaway rollers 144. The recessed portion 152 can be a curvilinear or curved surface that has a ramp on either side of the recessed portion 152, so that the torsional breakaway roller 144 can roll (in either direction) out of the recessed portion 152 in response to a certain amount of torque (e.g., greater than 40 ft. lbs.) is applied between the torsional breakaway spring 148 and the percutaneous post 104. In this manner, the user may feel a "pop" when the torsional breakaway roller 144 rolls out of the recessed portion 152. Thus, the torsional breakaway rollers 144 will then be biased to the curvilinear surface of the inner surface 150 of the torsional breakaway spring 148, which generates a greater force to the torsional breakaway spring 148 to restrict rotation of the torsional breakaway spring 148. This greater or increased force will consequently restrict rotation of the limb support housing 106 relative to the percutaneous post 104. In this way, the user may know that too much torque has been applied to the percutaneous post 104, so that the user can modify his/her behavior or task. Then, the user can grab and rotate the limb support housing 106 in the opposite direction until the one torsional breakaway roller 144 is re-seated into the recessed portion 152, thereby "popping" the prosthetic limb back into its intended/desired position.

The torsional breakaway spring 148 can be comprised of a rigid or semi-rigid material, such as a steel or aluminum (or another metal alloy), and can be sized and shaped having a relative thick wall, so that the torsional breakaway spring 148 is not necessary a spring in itself. The "spring" or "spring effect" aspect facilitated by the torsional breakaway spring 148 is because of the interface and functionality of the recessed portion 152 and the one torsional breakaway roller 144, which generates a spring effect when the one torsional breakaway roller 144 rolls along one curved side surface of the recessed portion 152 (depending on the direction of rotation). This is because if 20 ft. lbs., for instance, is required to unseat the torsional breakaway roller 144, and a torque of 17 ft. lbs. is applied, then the torsional breakaway roller 144 may slightly roll along one of the side curved surfaces of the recessed portion 152 (but not be completely unseated). Then, upon removal of the 17 ft. lbs. of torque, the torsional breakaway roller 144 may roll back into the recessed portion 152 in its proper or default position. Thus, the torsional breakaway roller 144, and the shape of the recessed portion 152, may define or provide some amount of compliance or spring effect in either rotational directions of the limb support housing 106 relative to the percutaneous post 104.

Note that two or more torsional breakaway rollers (e.g., 144) may be used in this system and one or more recessed portions (e.g., 152) may be formed into the inner surface 150. Further note that the torsional breakaway rollers 144 may be alternatively interfaced to the outer surface of the torsional breakaway spring 148, and similarly operate as described above to restrict or limit rotation of the limb support housing 106 relative to the percutaneous post 104.

Regarding the aforementioned bending release, the release housing assembly 140 of the quick-release device 100 can further comprise a plurality of roller seats 154 (6x) supported by and fastened to the limb support housing 106, as shown in FIG. 3A, about a peripheral area of the release housing assembly 140. FIG. 4 shows that each roller seat 154 can comprise a seat surface 156, which can be curved, curvilinear, or linear (if linear, it may formed at an inward angle). The release housing assembly 140 (FIG. 3A) can further comprise a bending breakaway spring 158 operable to flex or deflect to facilitate such bending release. A plurality of support brackets 160 can support a plurality of bending breakaway rollers 162 and can each be coupled to the bending breakaway spring 158. Note that the support bracket 160 and the bending breakaway roller 162 can together define a roller device 161. Further note that the bending breakaway spring 158 can be in the shape of a ring having a relatively large inner diameter and outer diameter relative to the thickness of the wall of the torsional breakaway spring 148, and can have a rectangular cross sectional area (or other shape, such as square, oval, polygon, irregular, etc.). Thus, in one example, the bending breakaway spring 158 can be considered "a ring spring" that is shaped like a ring that is capable of operating and deforming as a spring upon a load or force, as further detailed below.

As shown in FIGS. 3A and 4, each bending breakaway roller 162 can be seated in a respective seat surface 156 of a respective roller seat 154. The support brackets 160 can have an inwardly facing C-channel shape (FIG. 4) that receives and supports upper and lower surfaces of the bending breakaway spring 158, so that the entirety of the bending breakaway spring 158 is supported only by the support brackets 160. Note that the support brackets 160 are interfaced or coupled to the roller support plate 142, which is attached to the post receiving structure 110 (FIG. 3A).

Accordingly, in response to application of a bending moment between the percutaneous post support assembly 102 (FIG. 5) and the limb support housing 106, at least some of the bending breakaway rollers 162 are operable to cause a deformation force of the bending breakaway spring 158, which facilitates unseating of the plurality of bending breakaway rollers 162 from the roller seats 154 to pivotally release the limb support housing 106 (and the prosthesis) from the percutaneous post support assembly 102, as illustrated in FIG. 5. More particularly, during the bending moment, some of the bending breakaway rollers 162 will begin to roll up from their seats 154, which causes the bending breakaway rollers 162 to inwardly move (because of the inwardly shaped curvilinear surfaces of the seat 154). This inward movement of the bending breakaway rollers 162 causes the bending breakaway spring 158 to deform or deflect relative to the direction of the bending moment force (e.g., the bending breakaway spring 158 transitions from a circle to an oval shape or a circle with a smaller circumference). Such deformation of the bending breakaway spring 158 provides just enough clearance for such bending breakaway rollers 162 to become completely unseated from their respective roller seats 154, which releases the limb support housing 106 (and the prosthesis) from the percutaneous post support assembly 102. Thus, in one example, in response to application a bending moment (e.g., 42 ft. lbs.) in a plane orthogonal to the lengthwise axis of the percutaneous post 104, the limb support housing 106 may be released from the percutaneous post support assembly 102, because the bending release system is designed to release in response a defined amount of bending moment (e.g., 40 ft. lbs. or more), for instance. This provides a safety feature so that, when too much bending moment is applied, the prosthesis will release from the percutaneous post 104 to prevent damage to the device 100 and/or injury to the user.

Returning again to FIG. 4, the bending breakaway spring 158 can be comprised of a rigid or semi-rigid material (e.g., steel, aluminum, or a metal alloy), and can be shaped and sized having a relatively large diameter and thin wall, so that it deforms in response to the bending moment applied between the percutaneous post support assembly and the limb support housing. However, the material and shape and size of the bending breakaway spring 158 can be selected for a particular bending moment threshold, and the bending moment threshold can be dynamically modified by a user, as discussed below.

As best shown in FIG. 3A, the bending breakaway spring 158 and the torsional breakaway spring 148 can be substantially concentric, meaning that they can share a common centroid proximate or about the axis of rotation R1. The bending breakaway spring 158 can surround the torsional breakaway spring 148, meaning that the entirety of the torsional breakaway spring 148 is laterally situated within an inner area defined by the perimeter of the bending breakaway spring.

Note that each bending breakaway roller 162 operates about or has an axis of rotation that is transverse (e.g., orthogonal) to a longitudinal axis L1 that extends through the bending breakaway spring 158 (and the longitudinal axis L1 is congruent with the axis of rotation R1). Further note that the plurality of bending breakaway rollers 162 can comprise at least two bending breakaway rollers, such as the six shown, that surround the bending breakaway spring 158 and that are situated equidistance from each other around an outer surface of the bending breakaway spring 158.

Figure 7:
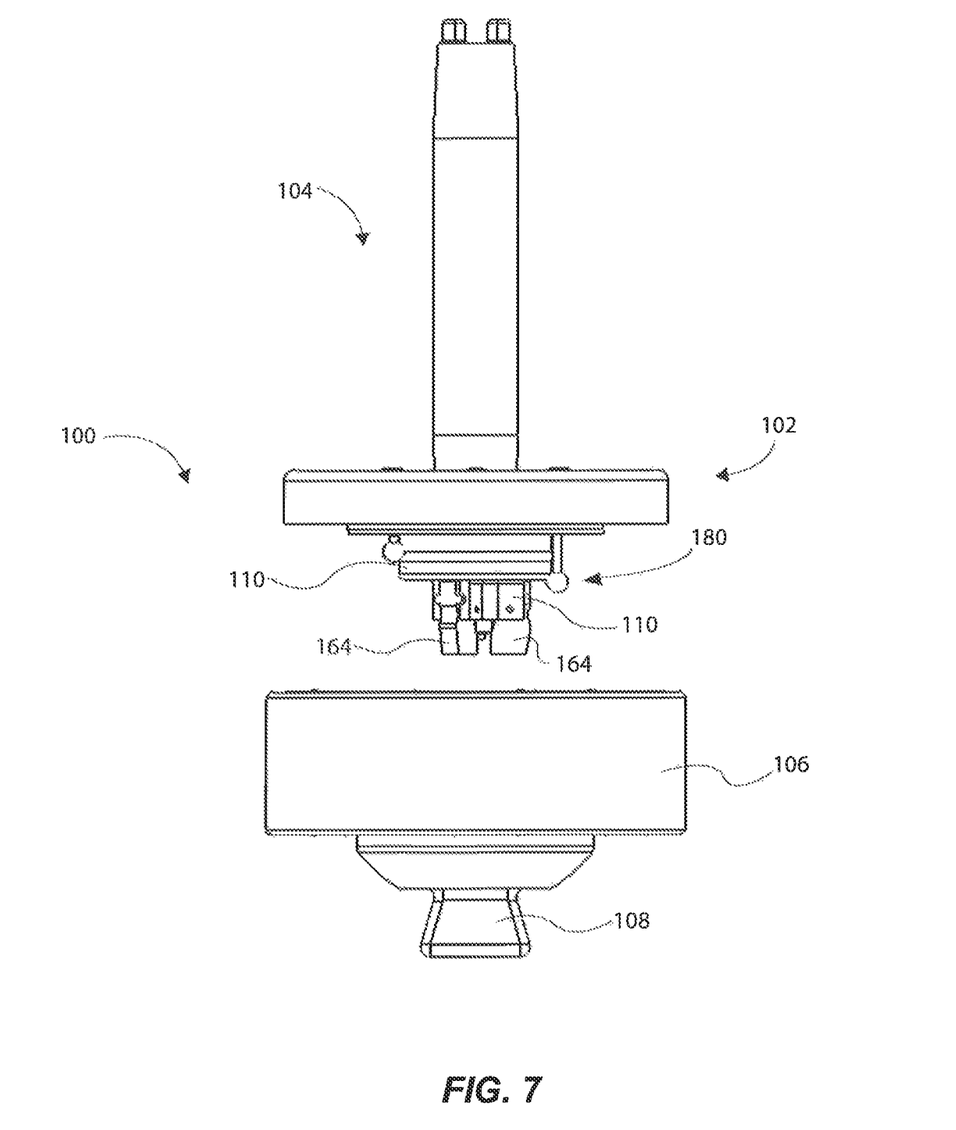
FIG. 7 is a side view of the quick-disconnect device of FIG. 1A, and showing axial release of a portion of the quick-disconnect device from the percutaneous post.

Regarding axial release of the limb support housing 106 (and the supported prosthesis) from the percutaneous post support assembly 102, FIG. 7 illustrates a position of such components after such axial release. More specifically, and with reference to FIG. 6, the quick-disconnect device 100 can comprise a plurality of seat bodies 164 supporting the post receiving structure 110 of the percutaneous post support assembly 102. A plurality of axial breakaway roller devices 166 (3x) can be slidably supported by the roller support 142 (FIG. 6), and each axial breakaway roller device 166 can comprise a roller support body 168 and a roller 170 seated in a respective seat body 164. The roller support bodies 168 can comprise a bracket or block that rotatably supports respective rollers 170, and each roller support body 168 is slidable along lower channels formed in the roller support 142 and in a radial direction towards and away from the longitudinal axis L1 during operation, as detailed below. A axial breakaway spring 172 can be operably coupled to each of the roller support bodies 168, as shown in FIG. 6, so that the roller support body 168 interfaces with and supports upper and lower surfaces of the axial breakaway spring 172. Thus, the entirety of the axial breakaway spring 172 is supported by and interfaced to the roller support bodies 168. Therefore, because of the compliant or spring-like nature of the axial breakaway spring 172, movement of the roller support bodies 168 facilitates deformation of the axial breakaway spring 172. Note that the axial breakaway spring 172 can be in the shape of a ring having a relatively large inner area or space relative to the thickness of the wall of the axial breakaway spring 172, and can have a rectangular cross sectional area (or other shape, such as square, oval, polygon, irregular, etc.). Thus, in one example, the axial breakaway spring 172 can be considered "a ring spring" that is shaped like a ring that is capable of operating and deforming as a spring upon a load or force, as further detailed below.

Accordingly, in response to application of an axial force between the percutaneous post support assembly 102 and the limb support housing 106 (along the longitudinal axis L1), the rollers 170 are caused to vertically roll along respective curvilinear surfaces 174 (FIG. 6) of the seat bodies 164, which causes the roller support bodies 168 to concurrently outwardly and radially slide out along lower channels of the roller support 142, which causes the plurality of roller devices 166 to collectively apply a radial force to the axial breakaway spring 172. Such radial force causes the axial breakaway spring 172 to deform, which provides sufficient clearance for each roller 170 to be unseated from the seat bodies 164, thereby axially releasing the percutaneous post support assembly 102 from the limb support housing 106. Once released, the user or individual can re-set the percutaneous post support assembly 102 back into the limb support housing 106 by axially pushing the seat bodies 164 down onto respective rollers 170, so that the rollers 170 can slide along respective inclined surfaces of the seat bodies 164 until being reseated in the curved surfaces of the seat bodies 164.

As shown best in FIG. 3A, the axial breakaway spring 172 can comprise an irregular ring shape or a serpentine ring shape having a plurality of curved or convoluted portions, or the axial breakaway spring can comprise a circular ring (like bending breakaway spring 158). The irregularly shaped axial breakaway spring 172 can be symmetrically formed, or can take other shapes. The axial breakaway spring 172 and the torsional breakaway spring 148, and the bending breakaway spring 158 can be substantially concentric, and the axial breakaway spring 172 can be situated within or surrounded by the torsional breakaway spring 148, such that the axial breakaway spring 172 is situated within an inner area defined by an inner surface of the torsional breakaway spring 148, as shown.

In some examples, the amount of force necessary to release the percutaneous post support assembly 102 from the limb support housing 106 is determined, at least partially, by the particular position, shape, and height of the particular seat surface that a particular roller rolls along to be unseated to facilitate such release. In one example, the configuration of the seat is adjustable, such as the case with roller seats 154 supported by the limb support housing 106. For instance, a set screw or other adjustment mechanism can be operated with a tool by a user or prosthetics medical professional to adjust the position of the roller seats 154, which thereby modifies the amount of compliance of the bending breakaway spring 158, which thereby modifies the bending moment threshold of a particular quick-release device. The same or similar configuration is possible with adjustment of the axial force required for axial release, specifically the seat bodies 164 can be moved or adjusted in position radially, so that a greater or lesser axial force is used to deflect the axial breakaway spring 172 to axially release the percutaneous post support assembly 102 from the limb support housing 106.

In one example, one or more tether devices 180 (FIG. 7) can be incorporated to prevent the limb support housing 106 from entirely being separated from the percutaneous post support assembly 102. The tether device 180 can include a ball attached to a cable (or rod), and the ball can be installed into a ball support portion of a component supported by the limb support housing 106. Thus, upon axial release (FIG. 7), the ball would remain supported by the limb support housing 106, while the cable would remain supported by the percutaneous post support assembly 102, so that the limb support housing 106 can "dangle" from the percutaneous post support assembly 102 by the cable. Another such tether device can be similarly incorporated for the bending release system discussed above.

In some examples, a particular quick-release device can include a magnet and a hall-effect sensor device to determine the displacement of one or more axial breakaway springs (i.e., 148, 158, 172) to provide an indication to a user regarding particular loads on components of the quick-release device. For instance, if the quick-release device was designed to release or breakaway upon a bending moment of 40 ft. lbs., such that the bending breakaway spring 158 would be deformed from nominal to about 2 mm, the sensor may detect a force at 30 ft. lbs. based on the sensed deflection of the ring spring (i.e., 1 mm), and then a computer system or other electronics system may cause an auditory signal to be heard by the user to provide indication that the maximum of 40 ft. lbs. is being reached, or can even cause a vibrational energy to be felt by the user via a vibrational device, or even cause a visual signal from a light source.

The quick-release device can be water and dirt resistant with the implementation of O-rings to seal leak paths, such as O-rings 186 and 188 (FIG. 6). Electrical conductors (not shown) may be routed through the device via channels of the percutaneous post 104, for instance, and then through areas of the quick-release device for control of prosthetic components, and to transmit data generated by sensors, such as myoelectrode sensors that gather electrical signals from movement of the user's muscles. This can include wireless control and monitoring of sensors.

Reference to a particular orientation of components is not meant to be limiting to a particular direction relative to ground or earth, such as vertical or horizontal or upper or lower.

The term "quick-disconnect" or "quick-connect" can mean that the quick-disconnect device (100 or 200) can be connected or disconnected to a percutaneous post by hand and without the use of tools (e.g., via the cam mechanism, or the lever device). The term "quick-disconnect" or "quick-connect" can also mean that some or all the components of the quick-disconnect device (100 or 200), such as the release housing assembly, can be connected or disconnected by hand, such as pushing the release housing assembly axially back into the percutaneous post support assembly 102 to re-seat the rollers 164 back into seats 174, and/or by pushing the limb support housing 106 at an angle to the percutaneous post support assembly 102 to re-seat the bending breakaway rollers 162 back into respective seat bodies 154. Moreover, if a torsional breakaway roller 144 has been unseated from recessed portion 152, a user can quickly, by hand, rotate the limb support housing 106 until one of the torsional breakaway rollers is re-seated into the recessed portion, which is another example of "quick-connect" contemplated herein.

The present disclosure sets forth a quick-disconnect device for a prosthetic limb comprising: a percutaneous post support assembly comprising a post locking assembly operable to attach the quick-disconnect device to a percutaneous post, a roller support coupled to the percutaneous post support assembly and a plurality of torsional breakaway rollers. A release housing assembly can be coupled to the percutaneous post support assembly, and can comprise a limb support housing supporting a limb attachment structure operable to support a prosthetic limb. The release housing assembly can comprise a torsional breakaway spring supported by the limb support housing, such that the torsional ring and the limb support housing are rotatable relative to the roller support.

The plurality of torsional breakaway rollers can be biased to a surface of the torsional breakaway spring to generate a spring force to restrict rotation of the limb support housing relative to the percutaneous post support assembly. In one example, a first torsional breakaway rollers of the plurality of torsional breakaway rollers is configured to be seated in a recessed portion of the torsional breakaway spring, such that the first torsional breakaway rollers is operable to be unseated from, or seated into, the recessed portion in response to a torque applied to the torsional breakaway spring.

In one example, the quick-disconnect device can further comprise a cam mechanism comprising at least one movable cam supported by the percutaneous post support assembly. The movable cam can be operable to lock or unlock the quick-disconnect device to the percutaneous post in response to rotation of a structural support housing of the percutaneous post support assembly relative to the limb support housing.

In one example, the quick-disconnect device can further comprise a movable lever supported by the percutaneous post support assembly, and can be operable to lock or unlock the quick-disconnect device to the percutaneous post.

In one example, the quick-disconnect device can further comprise a plurality of roller seats supported by the limb support housing, and a bending breakaway spring. A plurality of roller devices can be coupled to the bending breakaway spring, and each roller device can comprise a support bracket coupled to the bending breakaway spring, and a bending breakaway roller seated in a respective roller seat. In response to application of a bending moment between the percutaneous post support assembly and the limb support housing, at least some of the roller devices are operable to cause a deformation force of the bending breakaway spring, which facilitates unseating of the plurality of bending breakaway rollers from the roller seats to pivotally release the limb support housing from the percutaneous post support assembly.

In one example, the bending breakaway spring and the torsional breakaway spring are substantially concentric, and the bending breakaway spring may surround the torsional breakaway spring.

In one example, the bending breakaway spring can be comprised of a rigid or semi-rigid material that deform in response to a defined bending moment applied between the percutaneous post support assembly and the limb support housing.

In one example, the limb support housing defines a longitudinal axis that extends through a central area of the limb support housing, and each bending breakaway roller has an axis of rotation that is transverse to the longitudinal axis.

In one example, the plurality of roller devices comprises at least four roller devices that surround the bending breakaway spring and that are situated equidistance from each other around an outer surface of the bending breakaway spring.

In one example, the quick-disconnect device can further comprise a plurality of seat bodies supported by the percutaneous post support assembly, and a plurality of roller devices slidably supported by the roller support. Each roller device comprises a roller support body and a roller seated in a respective seat body. A axial breakaway spring can be operably coupled to each roller support body. In response to application of an axial force between the percutaneous post support assembly and the limb support housing, the rollers are operable to vertically roll along the respective seat bodies, which causes the roller support bodies to outwardly slide about the roller support, which causes the plurality of roller devices to collectively apply a radial force to the axial breakaway spring, thereby axially releasing the percutaneous post support assembly from the limb support housing upon the rollers being unseated.

In one example, the axial breakaway spring can comprise an irregular shape comprising a plurality of curved portions.

In one example, the rollers can be situated within an inner area defined by a perimeter of the axial breakaway spring.

In one example, the axial breakaway spring and the torsional breakaway spring can be substantially concentric, and the axial breakaway spring can be situated within an inner area defined by an inner surface of the torsional breakaway spring.

The present disclosure sets forth a quick-disconnect device for a prosthetic limb comprising a percutaneous post support assembly that can comprise a post locking assembly operable to attach the quick-disconnect device to a percutaneous post, and a roller support coupled to the percutaneous post support assembly and supporting a plurality of torsional breakaway rollers. A limb support housing can support the roller support, and can support a limb attachment structure operable to support a prosthetic limb. A torsional breakaway spring can be by the limb support housing, such that the torsional ring and the limb support housing are rotatable relative to the roller support. The plurality of torsional breakaway rollers can be spring biased to the torsional breakaway spring to restrict rotation of the limb support housing relative to the percutaneous post support assembly. A plurality of roller seats can be supported by the limb support housing. A plurality of bending breakaway rollers can be coupled to a bending breakaway spring, and each bending breakaway roller is seated in a respective roller seat. In response to application of a bending moment between the percutaneous post support assembly and the limb support housing, at least some of the bending breakaway rollers are operable to be unseated from the roller seats, which causes a deformation force of the bending breakaway spring, which facilitates pivotally release the limb support housing from the percutaneous post support assembly.

In one example, the quick-disconnect device can further comprise a plurality of seat bodies supported by the percutaneous post support assembly, and a plurality of roller devices slidably supported by the roller support. Each roller device can comprise a roller support body, and a roller seated in a respective seat body. A axial breakaway spring can be operably coupled to each roller support body. In response to application of an axial force between the percutaneous post support assembly and the limb support housing, the rollers are operable to vertically roll along the respective seat bodies, which causes the roller support bodies to outwardly slide about the roller support, which causes the plurality of roller devices to collectively apply a radial force to the axial breakaway spring, thereby axially releasing the percutaneous post support assembly from the limb support housing upon the rollers being unseated.

In one example, the axial breakaway spring, the torsional breakaway spring, and the bending breakaway spring are substantially concentric, and the bending breakaway spring can surround the torsional breakaway spring, and the torsional breakaway spring can surround the axial breakaway spring.

In one example, the torsional breakaway spring can comprise a recessed portion formed about an inner surface, and one of the torsional breakaway rollers can be seated in the recessed portion to provide compliance.

The present disclosure sets forth a quick-disconnect device for a prosthetic limb comprising a percutaneous post support assembly having a post locking assembly operable to attach the quick-disconnect device to a percutaneous post, and a limb support housing operably coupled to the percutaneous post support assembly, and supporting a limb attachment structure operable to support a prosthetic limb. The quick-disconnect device can comprise at least one bending breakaway spring, and a plurality of rollers operably with the at least one bending breakaway spring. In response to application of a load between the percutaneous post support assembly and the limb support housing, the plurality of rollers are operable to apply a force to the at least one bending breakaway spring to release the limb support housing from the percutaneous post support assembly.

In one example, the at least one axial breakaway spring comprises at least one of: a axial breakaway spring that facilitates axial release movement of the limb support housing from the percutaneous post support assembly; a torsional breakaway spring that facilitates torsional release movement of the limb support housing relative the percutaneous post support assembly; or a bending breakaway spring that facilities bending release movement of the limb support housing from the percutaneous post support assembly.

In one example, the quick-disconnect device can comprise a plurality of seats interfaced to respective rollers of the plurality of rollers. In response to the load, the rollers can be unseated from plurality of seats to facilitate release of the limb support housing from the percutaneous post support assembly.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

What is claimed is:

1. A quick-disconnect device for a prosthetic limb, comprising:
   a percutaneous post support assembly comprising a post locking assembly operable to attach the quick-disconnect device to a percutaneous post;
   a roller support coupled to the percutaneous post support assembly;
   a plurality of torsional breakaway rollers supported by the roller support;
   a release housing assembly coupled to the percutaneous post support assembly, and comprising a limb support housing supporting a limb attachment structure operable to support a prosthetic limb; and a torsional breakaway spring supported by the limb support housing, such that a torsional ring and the limb support housing are relatively rotatable using the roller support, wherein the plurality of torsional breakaway rollers are biased to a surface of the torsional breakaway spring to generate a spring force to restrict rotation of the limb support housing relative to the percutaneous post support assembly;

a plurality of roller seats supported by the limb support housing;

a bending breakaway spring;

a plurality of roller devices coupled to the bending breakaway spring, wherein each roller device comprises a support bracket coupled to the bending breakaway spring, and a bending breakaway roller seated in a respective roller seat; and wherein, in response to application of a bending moment between the percutaneous post support assembly and the limb support housing, at least some of the roller devices are operable to cause a deformation of the bending breakaway spring, which facilitates unseating of the bending breakaway rollers from the roller seats to pivotally release the limb support housing from the percutaneous post support assembly, wherein the bending breakaway spring and the torsional breakaway spring are substantially concentric, and the bending breakaway spring surrounds the torsional breakaway spring.

2. The quick-disconnect device as in claim 1, wherein a first torsional breakaway rollers of the plurality of torsional breakaway rollers is configured to be seated in a recessed portion of the torsional breakaway spring, such that the first torsional breakaway rollers is operable to be unseated from, or seated into, the recessed portion in response to a torque.

3. The quick-disconnect device as in claim 1, wherein further comprising a cam mechanism comprising at least one movable cam supported by the percutaneous post support assembly, wherein the movable cam is operable to lock or unlock the quick-disconnect device to the percutaneous post in response to rotation of a structural support housing of the percutaneous post support assembly relative to the limb support housing.

4. The quick-disconnect device as in claim 1, further comprising a movable lever supported by the percutaneous post support assembly, wherein the movable lever is operable to lock or unlock the quick-disconnect device to the percutaneous post.

5. The quick-disconnect device as in claim 1, wherein the bending breakaway spring is comprised of a rigid or semi-rigid material that deforms in response to a defined bending moment applied between the percutaneous post support assembly and the limb support housing.

6. The quick-disconnect device as in claim 1, wherein the limb support housing defines a longitudinal axis that extends through a central area of the limb support housing, wherein each bending breakaway roller has an axis of rotation that is transverse to the longitudinal axis.

7. The quick-disconnect device as in claim 1, wherein the plurality of roller devices comprises at least two roller devices that surround the bending breakaway spring and that are situated equidistance from each other around an outer surface of the bending breakaway spring.

8. The quick-disconnect device as in claim 1, further comprising:

a plurality of seat bodies supported by the percutaneous post support assembly;

a plurality of breakaway rollers slidably supported by the roller support, each breakaway roller comprising a roller support body, and a roller seated in a respective seat body; and an axial breakaway spring operably coupled to each roller support body, wherein, in response to application of an axial force between the percutaneous post support assembly and the limb support housing, the rollers are operable to vertically roll along the respective seat bodies, which causes the roller support bodies to outwardly slide about the roller support, which causes the plurality of breakaway rollers to collectively apply a force to the axial breakaway spring, thereby axially releasing the percutaneous post support assembly from the limb support housing upon the rollers being unseated.

9. The quick-disconnect device as in claim 8, wherein the axial breakaway spring comprises a shape comprising a plurality of curved portions.

10. The quick-disconnect device as in claim 8, wherein the plurality of breakaway rollers are situated within an area defined by a perimeter of the axial breakaway spring.

11. The quick-disconnect device as in claim 8, wherein the axial breakaway spring and the torsional breakaway spring are substantially concentric, and wherein the axial breakaway spring is situated within an area defined by an inner surface of the torsional breakaway spring.

12. A quick-disconnect device for a prosthetic limb, comprising:

a percutaneous post support assembly comprising a post locking assembly operable to attach the quick-disconnect device to a percutaneous post;

a roller support coupled to the percutaneous post support assembly and supporting a plurality of torsional breakaway rollers;

a limb support housing supporting the roller support, and supporting a limb attachment structure operable to support a prosthetic limb;

a torsional breakaway spring supported by the limb support housing, such that a torsional ring and the limb support housing are rotatable relative to the roller support, wherein the plurality of torsional breakaway rollers are spring biased to the torsional breakaway spring to restrict rotation of the limb support housing relative to the percutaneous post support assembly;

a plurality of roller seats supported by the limb support housing;

a bending breakaway spring;

a plurality of bending breakaway rollers coupled to the bending breakaway spring, wherein each bending breakaway roller is seated in a respective roller seat, wherein at least some of the bending breakaway rollers are operable to be unseated from the roller seats, which pivotally releases the limb support housing from the percutaneous post support assembly;

a plurality of seat bodies supported by the percutaneous post support assembly;

a plurality of roller devices slidably supported by the roller support, each roller device comprising a roller support body, and a roller seated in a respective seat body; and an axial breakaway spring operably coupled to each roller support body, wherein, in response to application of an axial force between the percutaneous post support assembly and the limb support housing, the rollers are operable to vertically roll along the respective seat bodies, which causes the roller support bodies to outwardly slide about the roller support, which causes the plurality of roller devices to collectively apply a force to the axial breakaway spring, thereby axially releasing the percutaneous post support assembly from the limb support housing upon the rollers being unseated, wherein the axial breakaway spring, the torsional breakaway spring, and the bending breakaway spring are substantially concentric, and the bending breakaway spring surrounds the torsional breakaway spring, and wherein the torsional breakaway spring surrounds the axial breakaway spring.

13. A quick-disconnect device for a prosthetic limb, comprising:
    a percutaneous post support assembly having a post locking assembly operable to attach the quick-disconnect device to a percutaneous post;
    a limb support housing operably coupled to the percutaneous post support assembly, and supporting a limb attachment structure operable to support a prosthetic limb;
    at least one bending breakaway spring; and
    a plurality of rollers operable with the at least one bending breakaway spring,
    wherein, in response to application of a load between the percutaneous post support assembly and the limb support housing, the plurality of rollers are operable to apply a load to the at least one bending breakaway spring to release the limb support housing from the percutaneous post support assembly; and
    a torsional breakaway spring that facilitates torsional release movement of the limb support housing relative the percutaneous post support assembly,
    wherein the torsional breakaway spring comprises a recessed portion formed about an inner surface, and at least one torsional breakaway roller is seated in the recessed portion to provide compliance.

14. The quick-disconnect device as in claim 13, further comprising a plurality of seats interfaced to respective rollers of the plurality of rollers, wherein, in response to the load, the rollers are unseated from plurality of seats to facilitate release of the limb support housing from the percutaneous post support assembly.

15. A quick-disconnect device for a prosthetic limb, comprising:
    a percutaneous post support assembly comprising a post locking assembly operable to attach the quick-disconnect device to a percutaneous post;
    a roller support coupled to the percutaneous post support assembly;
    a plurality of torsional breakaway rollers supported by the roller support;
    a release housing assembly coupled to the percutaneous post support assembly, and comprising a limb support housing supporting a limb attachment structure operable to support a prosthetic limb;
    a torsional breakaway spring supported by the limb support housing, such that a torsional ring and the limb support housing are relatively rotatable using the roller support,
    wherein the plurality of torsional breakaway rollers are biased to a surface of the torsional breakaway spring to generate a spring force to restrict rotation of the limb support housing relative to the percutaneous post support assembly; and
    wherein a first torsional breakaway roller of the plurality of torsional breakaway rollers is configured to be seated in a recessed portion of the torsional breakaway spring, such that a torsional breakaway roller is operable to be unseated from, or seated into, the recessed portion in response to torque.

16. A quick-disconnect device for a prosthetic limb, comprising:
    a percutaneous post support assembly comprising a post locking assembly operable to attach the quick-disconnect device to a percutaneous post;
    a roller support coupled to the percutaneous post support assembly and supporting a plurality of torsional breakaway rollers;
    a limb support housing supporting the roller support, and supporting a limb attachment structure operable to support a prosthetic limb;
    a torsional breakaway spring supported by the limb support housing, such that a torsional ring and the limb support housing are rotatable relative to the roller support, wherein the plurality of torsional breakaway rollers are spring biased to the torsional breakaway spring to restrict rotation of the limb support housing relative to the percutaneous post support assembly;
    a plurality of roller seats supported by the limb support housing;
    a bending breakaway spring;
    a plurality of bending breakaway rollers coupled to the bending breakaway spring, wherein each bending breakaway roller is seated in a respective roller seat, wherein at least some of the bending breakaway rollers are operable to be unseated from the roller seats, which pivotally releases the limb support housing from the percutaneous post support assembly; and
    wherein the torsional breakaway spring comprises a recessed portion formed about an inner surface, and wherein one of the torsional breakaway rollers is seated in the recessed portion to provide compliance.

* * * * *